(12) United States Patent
Mallo et al.

(10) Patent No.: US 6,346,239 B1
(45) Date of Patent: *Feb. 12, 2002

(54) USE IN COSMETICS OF A REVERSE LATEX OF NITROGENOUS SALTS OF POLYACRYLATE, NOVEL LATICES, PROCESS FOR THEIR PREPARATION AND COSMETIC COMPOSITIONS INCORPORATING THEM

(75) Inventors: Paul Mallo, Chatou; Guy Tabacchi, Castres; Jean Pierre Boiteux, Saix, all of (FR)

(73) Assignee: Societe d'Exploitation de Produits Pour les Industries Chimques Seppic, Paris Cedex (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/466,185

(22) Filed: Dec. 17, 1999

(30) Foreign Application Priority Data

Dec. 18, 1998 (FR) .............................................. 98 16039
Feb. 9, 1999 (FR) .............................................. 99 01497

(51) Int. Cl.$^7$ ............................. A61K 6/00; A61K 7/00; A61K 7/06; A61K 7/11
(52) U.S. Cl. .................. 424/70.16; 424/70.1; 424/401; 514/844; 514/939; 514/944; 514/945
(58) Field of Search ................................ 424/70.1, 401, 424/70.16; 514/844, 939, 944, 945

(56) References Cited

U.S. PATENT DOCUMENTS 5,185,395 A    2/1993   Robinson et al. ........... 524/457

FOREIGN PATENT DOCUMENTS

| EP | 0 196 162 | * | 2/1986 |
| EP | 0 186 361 |   | 7/1986 |
| EP | 0 503 853 | * | 9/1992 |
| FR | 2 710 263 |   | 3/1995 |

* cited by examiner

Primary Examiner—Thurman K. Page
Assistant Examiner—Todd D Ware
(74) Attorney, Agent, or Firm—Young & Thompson

(57) ABSTRACT

Use of a composition having an oil phase, an aqueous phase, at least one emulsifier of water-in-oil (W/O) type and at least one emulsifier of oil-in-water (O/W) type, in the form of a reverse latex comprising from 20% to 70% by weight, and preferably from 25% to 40% by weight, of an anionic polyelectrolyte, the anionic polyelectrolyte being based on partially neutralized acrylic acid, which may be branched and/or crosslinked, to prepare a cosmetic, dermopharmaceutical or pharmaceutical composition. Novel lattices, process for their preparation and cosmetic, dermopharmaceutical or pharmaceutical composition incorporating them.

11 Claims, No Drawings

USE IN COSMETICS OF A REVERSE LATEX OF NITROGENOUS SALTS OF POLYACRYLATE, NOVEL LATICES, PROCESS FOR THEIR PREPARATION AND COSMETIC COMPOSITIONS INCORPORATING THEM

BACKGROUND OF THE INVENTION

The present patent application relates to thickening water-in-oil latices, to a process for their preparation and to their use as thickeners and/or emulsifiers for skincare and haircare products or for the manufacture of cosmetic, dermopharmaceutical or pharmaceutical preparations.

DESCRIPTION OF THE RELATED ART

Various thickeners exist and are already used for these purposes. Natural products such as guar gums or starch are known in particular, but the drawbacks thereof are those inherent in natural products, such as currency fluctuations, difficulties in supply and a random quality.

Synthetic polymers in powder form, mainly polyacrylic acids, are also widely used but have the drawback of requiring neutralization during use, since they only develop their viscosity from a pH of greater than 6.5 and they are often difficult to dissolve.

Synthetic thickening polymers which are in the form of reverse latices, i.e. latices in which the continuous phase is an oil, also exist. These latices dissolve extremely quickly; the polymers contained in these reverse latices are usually acrylamide/alkali metal acrylate or acrylamide/sodium 2-acrylamido-2-methylpropanesulphonate copolymers; they are already neutralized and, when dissolved in water, for example to a concentration of 1%, it is observed that the pH is generally greater than 6.

However, acrylamide/sodium acrylate copolymers do not develop considerable thickening properties when the pH is lowered below 6; on the other hand, the acrylamide/sodium 2-acrylamido-2-methylpropane-sulphonate copolymers described in EP 0 503 853 conserve considerable thickening capacity even at a pH equal to 4.

However, such copolymers have monoacrylamide contents which, although extremely low, may lead in the future to their use in cosmetics not being possible, on account of the changes in European regulations regarding hazardous substances.

Furthermore, all of the polymers mentioned have a tendency to lose their thickening property when the medium to be thickened, for example a cosmetic product, contains salts; this tendency becomes accentuated as the concentration of salts present in the said medium increases.

SUMMARY OF THE INVENTION

The Applicant has thus become interested in the search for novel acrylamide-free reverse emulsions which are more stable with respect to electrolytes.

According to a first aspect of the present invention, its subject is the use of a composition comprising an oil phase, an aqueous phase, at least one emulsifier of water-in-oil (W/O) type and at least one emulsifier of oil-in-water (O/W) type, in the form of a reverse latex comprising from 20% to 70% by weight, and preferably from 25% to 40% by weight, of an anionic polyelectrolyte, the said anionic polyelectrolyte being based on partially neutralized acrylic acid, which may be branched and/or crosslinked, to prepare a cosmetic, dermopharmaceutical or pharmaceutical composition.

DESCRIPTION OF THE PREFERRED EMBODIMENTS

The expression "emulsifier of water-in-oil type" denotes emulsifiers with an HLB value which is low enough to give water-in-oil emulsions, such as the surfactant polymers sold under the name Hypermer™ or such as sorbitan esters, for instance sorbitan monooleate sold by the company SEPPIC under the name Montane™ 80 or sorbitan isostearate sold by SEPPIC under the name Montane™ 70.

The expression "emulsifier of the oil-in-water type" denotes emulsifiers with an HLB value which is high enough to give oil-in-water emulsions, such as, for example, ethoxylated sorbitan esters, for instance sorbitan oleate ethoxylated with 20 mol of ethylene oxide or sorbitan laurate ethoxylated with 20 mol of ethylene oxide, sold by the company SEPPIC under the names Montanox™ 80 and Montanox™ 20, respectively, castor oil ethoxylated with 40 mol of ethylene oxide or alternatively lauryl alcohol ethoxylated with 7 mol of ethylene oxide, sold by the company SEPPIC under the names Simulsol™ OL 50 and Simulsol™ P7, respectively.

The expression "partially neutralized acrylic acid" denotes more particularly acrylic acid partially salified in the form of an alkali salt, such as the sodium or potassium salt, or in the form of the salt of a nitrogenous base, such as the ammonium salt, or a salt with a compound containing quaternary ammonium, such as an amino alcohol salt. It is preferably acrylic acid partially neutralized in the form of the ammonium salt ($NH_4^+$) or a monoethanolamine salt ($HOCH_2CH_2NH_3^+$).

The expression "branched polymer" denotes a non-linear polymer which contains pendant chains so as to obtain, when this polymer is dissolved in water, a strong state of entanglement leading to very high low-gradient viscosities.

The expression "crosslinked polymer" denotes a non-linear polymer which is in the form of a three-dimensional network which is insoluble in water but swellable in water and thus leads to the production of a chemical gel.

The composition according to the invention can comprise crosslinked units and/or branched units.

The term "amino alcohol" means mono- or poly (hydroxyalkyl)amines.

A subject of the invention is, more particularly, the use, as defined above, of a composition in which the anionic polyelectrolyte is crosslinked and/or branched with a crosslinking agent and/or a branching agent chosen from trimethylolpropane triacrylate, ethylene glycol dimethacrylate or methylenebis(acrylamide) or compounds comprising at least two allyl radicals such as, for example, diallyloxyacetic acid or a salt thereof such as sodium diallyloxyacetate, triallylamine or diallylurea.

The crosslinking and/or branching agent is generally used in a molar proportion, expressed relative to the monomers used, of from 0.05% to 0.5% and preferably from 0.1% to 0.25%.

The latex according to the invention generally contains from 2.5% to 15% by weight and preferably from 4% to 9% by weight, of emulsifiers, among which from 20% to 50%, in particular from 25% to 40%, of the total weight of the emulsifiers present are of the water-in-oil (W/O) type and in which from 80% to 50%, in particular from 75% to 60%, of the total weight of the emulsifiers are of the oil-in-water (O/W) type.

According to one specific aspect of the present invention, the oil phase of the composition used represents from 15% to 40%, preferably from 20% to 25%, of the total weight of this composition.

This oil phase consists either of a commercial mineral oil containing saturated hydrocarbons of paraffin, isoparaffin or cycloparaffin type, with a density at room temperature of between 0.7 and 0.9 and a boiling point of greater than 180° C., such as, for example, Exxol™ D 100 S sold by Exxon or a white mineral oil such as Marcol™ 52 also sold by Exxon, the isohexadecane sold by Bayer or isododecane, or of a plant oil such as hexamethyltetracosane or squalane, or of a synthetic oil such as polyisobutene or hydrogenated polyisobutene, or of a mixture of several of these oils.

The isohexadecane, which is identified in Chemical Abstracts by the number RN=93685-80-4, is a mixture of $C_{12}$, $C_{16}$ and $C_{20}$ isoparaffins containing at least 97% $C_{16}$ isoparaffins, among which the main constituent is 2,2,4,4,6,8,8-heptamethylnonane (RN=4390-04-9). It is sold in France by the company Bayer. Marcol™ 52 is a commercial oil corresponding to the definition of liquid petroleum jellies in the French Codex. It is a white mineral oil in accordance with the rules FDA 21 CFR178.878 and CFR 178.3620(a); it is registered in volume US XXIII of the USA Pharmacopoeia (1995) and in the European Pharmacopoeia (1993).

According to one preferred aspect of the present invention, the oil phase of the composition used comprises isohexadecane or a white mineral oil.

The latices contain between 20% and 50% water. They can also contain various additives such as complexing agents, transfer agents or chain-limiting agents.

According to a second aspect of the present invention, its subject is a composition as employed in the use defined above, comprising an oil phase, an aqueous phase, at least one emulsifier of water-in-oil (W/O) type and at least one emulsifier of oil-in-water (O/W) type, in the form of a reverse latex comprising from 20% to 70% by weight, and preferably from 25% to 40% by weight, of a crosslinked anionic polyelectrolyte, the said anionic polyelectrolyte being based on partially neutralized acrylic acid, characterized in that the crosslinking agent is chosen from compounds comprising at least two allyl radicals and most particularly from diallyloxyacetic, sodium diallyloxyacetate or triallylamine.

According to a third aspect of the present invention, its subject is a composition as employed in the use defined above, comprising an oil phase, an aqueous phase, at least one emulsifier of water-in-oil (W/O) type and at least one emulsifier of oil-in-water (O/W) type, in the form of a reverse latex comprising from 20% to 70% by weight, and preferably from 25% to 40% by weight, of an anionic polyelectrolyte which may be branched and/or crosslinked, characterized in that the said anionic polyelectrolyte is based on partially neutralized acrylic acid, in the form of an amino alcohol salt, and preferably a monoethanolamine salt.

According to a fourth aspect of the present invention, its subject is also a process for preparing the composition as defined above, characterized in that:
a) an aqueous solution containing the monomers and the optional additives is emulsified in an oil phase in the presence of one or more emulsifiers of water-in-oil type,
b) the polymerization reaction is initiated by introducing a free-radical initiator and optionally a co-initiator into the emulsion formed in a), after which the reaction is left to proceed,
c) when the polymerization reaction is complete, one or more emulsifiers of oil-in-water type are introduced at a temperature below 50° C.

According to one variant of this process, the reaction medium obtained from step b) is concentrated by distillation before step c) is carried out.

According to a preferred embodiment of the process as defined above, the polymerization reaction is initiated by a redox couple which generates hydrogen sulphite ions ($HSO_3^-$), such as the cumene hydroperoxide/sodium metabisulphite ($Na_2S_2O_5$) couple the sodium, potassium or ammonium peroxydisulphate/sodium metabisulphite or the cumene hydroperoxide/thionyl chloride ($SOCl_2$) couple, at a temperature below or equal to 10° C., if desired accompanied by a polymerization co-initiator such as, for example, azobis(isobutyronitrile), followed by proceeding either under virtually adiabatic conditions up to a temperature of greater than or equal to 50° C., or by controlling the temperature.

A subject of the invention is also a cosmetic, dermopharmaceutical or pharmaceutical composition, characterized in that it comprises at least one reverse latex as defined above, as well as a process for preparing a cosmetic, dermopharmaceutical or pharmaceutical composition, characterized in that from 0.1% to 1% by weight of a composition whose use is the subject matter of the present invention is incorporated therein.

The cosmetic, dermopharmaceutical or pharmaceutical composition defined above generally comprises from 0.1% to 10%, and more particularly between 0.5% and 5%, by weight of the said reverse latex. It is, in particular, in the form of a milk, a lotion, a gel, a cream, a soap, a bubble bath, a balm, a shampoo or a conditioner.

In general, the said reverse latex can advantageously replace the products sold under the name Sepigel™ 305 or Sepigel™ 501 by the Applicant, in cosmetic, dermopharmaceutical or pharmaceutical compositions, since it also has good compatibility with the other excipients used for the preparation of formulations such as milks, lotions, creams, soaps, bubble baths, balms, shampoos or conditioners. It can also be used in combination with the said Sepigel products. In particular, it is compatible with the concentrates described and claimed in the international publications WO 92/06778, WO 95/04592, WO 95/13863, WO 98/47610 or FR 2 734 496, or with the surfactants described in WO 93/08204.

It is also compatible with Montanov™ 68, Montanov™ 82, Montanov™ 202 and Sepiperl™ N.

It can be used in emulsions of the type described and claimed in EP 0 629 396 and in cosmetically or physiologically acceptable aqueous dispersions with an organopolysiloxane compound chosen, for example, from those described in WO 93/05762 or in WO 93/21316. It can also be used to form cosmetically or physiologically acceptable aqueous gels at acidic pH, such as those described in WO 93/07856; it can also be used in combination with nonionic celluloses, for example to form styling gels, such as those described in EP 0 684 024, or alternatively in combination with fatty acid esters of sugars, to form compositions for treating the hair or the skin, such as those described in EP 0 603 019, or alternatively in shampoos or conditioners as described and claimed in WO 92/21316, or, finally, in combination with an anionic homopolymer such as Carbopol™ or Pemulen™, to form products for treating the hair, such as those described in DE 195 23596.

It is also compatible with many active principles, such as, for example, self-tanning agents such as dihydroxyacetone (DHA) or anti-acne agents; it can thus be introduced into self-tanning compositions such as those claimed in EP 0 715 845, EP 0 604 249, EP 0 576 188 or in WO 93/07902.

It is also compatible with N-acylamino acid derivatives, thereby allowing it to be used in soothing compositions, in particular for sensitive skin, such as those described or claimed in WO 92/21318, WO 94/27561 or WO 98/09611.

It is also compatible with glycolic acids, with lactic acid, with salicylic acid, retinoids, phenoxyethanol, sugars, glyceraldehyde, xanthans, fruit acids and the various polyols used in the manufacture of cosmetic formulations.

The composition according to the invention is, most particularly, compatible with cosmetic active agents that are rich in mineral salts, for example in sodium or magnesium salts. It is compatible in particular with Sepicalm™ S, Sepicontrol™ A5, sodium 2-pyrrolidonecarboxylate, Proteol™ OAT, Ajidew™ A100 or pyrrolidone.

Finally, a subject of the invention is a cosmetic, dermopharmaceutical or pharmaceutical composition as defined above and containing up to 5% by weight of one or more metal cations chosen in particular from sodium, potassium, magnesium, manganese and aluminium cations.

The examples which follow are intended to illustrate the present invention without, however, limiting it.

EXAMPLE 1

Reverse-latex Preparations

Example 1a)

Procedure

The following are placed in a beaker with stirring:
250 g of deionized water,
250 g of glacial acrylic acid,
30% aqueous ammonia solution so as to bring the pH of the solution to 5.5, i.e. about 170 g,
0.45 g of a commercial 40% sodium diethylenetriaminepentaacetate solution,
2.31 g of a commercial 50% sodium diallyloxyacetate solution,
the mixture is made up to 682 g with deionized water.

In parallel, an organic phase is prepared by introducing the following successively into a beaker with stirring:
220 g of isohexadecane,
30 g of Montane™ 80 VG (sorbitan oleate sold by the company SEPPIC),
0.2 g of AIBN.

The aqueous phase is gradually introduced into the organic phase and is then subjected to vigorous mechanical stirring with an Ultra-Turrax™ machine sold by IKA. The emulsion obtained is then transferred into a polymerization reactor. A large amount of nitrogen is bubbled through the emulsion to remove the oxygen, followed by cooling to 5–6° C.

0.16 g of sodium peroxydisulphate diluted in 20 g of water are then introduced.

After a sufficient time to obtain good homogenization of the solution, an aqueous sodium metabisulphite solution (0.2 g/100 ml of water) is then introduced over 60 minutes at a rate of 0.5 ml/minute.

The reaction medium is maintained at this temperature for 90 minutes.

The resulting mixture is then cooled to about 35° C., after which 50 g of Simulsol™ OL50 are added to obtain the desired emulsion.

Evaluation of the properties of the latex obtained
viscosity at 25° C. of the latex at 3% in water (Brookfield RVT, rotor No. 6, speed 20): η=30,500 mPa.s;
viscosity at 25° C. of the latex at 3% in water (Brookfield RVT, rotor No. 6, speed 5): η=93,000 mPa.s;
viscosity at 25° C. of the latex at 3% in water +0.1% NaCl (Brookfield RVT, rotor No. 6, speed 5): η=20,200 mPa.s;
viscosity at 25° C. of the latex at 3% in water +0.1% NaCl (Brookfield RVT, rotor No. 6, speed 20): η=7600 mPa.s;

Example 1b)

Working as in Example 1a), but introducing 50 g of lauryl alcohol ethoxylated with 7 mol of ethylene oxide, instead of the Simulsol™ OL 50, a latex is obtained which has equivalent viscometric properties.

Example 1c)

Working as in Example 1a), but using 0.95 g of triallylamine instead of the 2.31 g of commercial 50% sodium diallyloxyacetate solution, a latex is obtained which has the following viscometric properties:
viscosity at 25° C. of the latex at 3% in water (Brookfield RVT, rotor No. 6, speed 20): η=36,200 mPa.s;
viscosity at 25° C. of the latex at 3% in water (Brookfield RVT, rotor No. 6, speed 5): η=108,000 mPa.s;
viscosity at 25° C. of the latex at 3% in water +0.1% NaCl (Brookfield RVT, rotor No. 6, speed 5): η=16,000 mPa.s;
viscosity at 25° C. of the latex at 3% in water +0.1% NaCl (Brookfield RVT, rotor No. 6, speed 20): η=6200 mPa.s;

Example 1d)

Procedure

The following are placed in a beaker with stirring:
250 g of deionized water,
250 g of glacial acrylic acid,
149.6 g of monoethanolamine, so as to bring the pH of the solution to 5.5;
0.45 g of commercial 40% sodium diethylenetriaminepentaacetate solution,
3.4 g of commercial 50% sodium diallyloxyacetate solution,
the mixture is made up to 682 g with deionized water.

In parallel, an organic phase is prepared by successively introducing the following into a beaker with stirring:
220 g of isohexadecane,
30 g of Montane™ 80 VG (sorbitan oleate sold by the company SEPPIC),
0.2 g of AIBN.

The aqueous phase is gradually introduced into the organic phase and is then subjected to vigorous mechanical stirring using an Ultra-Turrax™ machine, sold by IKA. The emulsion obtained is then transferred into a polymerization reactor. A large amount of nitrogen is bubbled through the emulsion to remove the oxygen, followed by cooling to 5–6° C.

0.54 g of sodium peroxydisulphate diluted in 20 g of water is then introduced.

After a sufficient time to obtain good homogenization of the solution, an aqueous sodium metabisulphite solution (0.4 g/100 ml of water) is then introduced over 60 minutes at a rate of 0.5 ml/minute.

The reaction medium is maintained at this temperature for 90 minutes.

The mixture is then cooled to about 35° C., followed by addition of 50 g of Laureth-7 to obtain the desired emulsion.

Evaluation of the Properties of the Latex Obtained
viscosity at 25° C. of the latex at 3% in water (Brookfield RVT, rotor No. 6, speed 20): η=23,800 mPa.s;
viscosity at 25° C. of the latex at 3% in water (Brookfield RVT, rotor No. 6, speed 5): η=69,800 mPa.s;

viscosity at 25° C. of the latex at 3% in water +0.1% NaCl (Brookfield RVT, rotor No. 6, speed 5): $\eta$=28,000 mPa.s;

viscosity at 25° C. of the latex at 3% in water +0.1% NaCl (Brookfield RVT, rotor No. 6, speed 20): $\eta$=10,200 mPa.s.

Example 1e)

Working as in Example 1d), but using 0.215 g of methylenebis(acrylamide) instead of the 3.40 g of commercial 50% sodium diallyloxyacetate solution, a latex is obtained which has the following viscometric properties:

viscosity at 25° C. of the latex at 3% in water (Brookfield RVT, rotor No. 6, speed 20): $\eta$=30,400 mPa.s;

viscosity at 25° C. of the latex at 3% in water (Brookfield RVT, rotor No. 6, speed 5): $\eta$=92,000 mPa.s;

viscosity at 25° C. of the latex at 3% in water +0.1% NaCl (Brookfield RVT, rotor No. 6, speed 5): $\eta$=23,000 mPa.s;

viscosity at 25° C. of the latex at 3% in water +0.1% NaCl (Brookfield RVT, rotor No. 6, speed 20): $\eta$=8600 mPa.s.

Example 1f)

Working as in Example 1d), but using 0.039 g of cumene hydroperoxide instead of the 0.54 g of sodium peroxydisulphate diluted in 20 g of water and 50 g of Simulsol™ OL 50 instead of the 50 g of Simulsol™ P7, a latex is obtained which has the following viscometric properties:

viscosity at 25° C. of the latex at 3% in water (Brookfield RVT, rotor No. 6, speed 20): $\eta$=37,200 mPa.s;

viscosity at 25° C. of the latex at 3% in water (Brookfield RVT, rotor No. 6, speed 5): $\eta$=114,000 mPa.s;

viscosity at 25° C. of the latex at 3% in water +0.1% NaCl (Brookfield RVT, rotor No. 6, speed 20): $\eta$=12,000 mPa.s;

viscosity at 25° C. of the latex at 3% in water +0.1% NaCl (Brookfield RVT, rotor No. 6, speed 5): $\eta$=35,000 mPa.s.

The examples which follow use, without discrimination, one of the compositions prepared in 1a to 1f (referred to as composition 1).

EXAMPLE 2

Care cream

| | |
|---|---|
| Cyclomethicone: | 10% |
| Composition 1: | 0.8% |
| Montanov ™ 68: | 2% |
| Stearyl alcohol: | 1.5% |
| Preserving agent: | 0.65% |
| Lysine: | 0.025% |
| EDTA (disodium salt): | 0.05% |
| Xanthan gum: | 0.2% |
| Glycerol: | 3% |
| Water: | qs 100% |

EXAMPLE 3

Care cream

| | |
|---|---|
| Cyclomethicone: | 10% |
| Composition 1: | 0.8% |
| Montanov ™ 68: | 2% |
| Perfluoropolymethyl isopropyl ether: | 0.5% |
| Stearyl alcohol: | 1.5% |
| Preserving agent: | 0.65% |
| Lysine: | 0.025% |
| EDTA (disodium salt): | 0.05% |
| Pemulen ™ TR1: | 0.2% |
| Glycerol: | 3% |
| Water: | qs 100% |

EXAMPLE 4

After-shave Balm

Formula

| | | |
|---|---|---|
| A | Composition 1: | 1.5% |
| | Water: | qs 100% |
| B | Micropearl ™ M 100: | 5.0% |
| | Sepicide ™ M CI: | 0.50% |
| | Fragrance: | 0.20% |
| | 95° ethanol: | 10.0% |

Procedure

Add B to A.

EXAMPLE 5

Satin Emulsion for the Body

Formula

| | | |
|---|---|---|
| A | Simulsol ™ 165: | 5.0% |
| | Lanol ™ 1683: | 8.50% |
| | Karite butter: | 2% |
| | Liquid paraffin: | 6.5% |
| | Lanol ™ 14M: | 3% |
| | Lanol ™ S: | 0.6% |
| B | Water: | 66.2% |
| C | Micropearl ™ M 100: | 5% |
| D | Composition 1: | 3% |
| E | Sepicide ™ CI: | 0.3% |
| | Sepicide ™ HB: | 0.5% |
| | Monteine ™ CA: | 1% |
| | Fragrance: | 0.20% |
| | Vitamin E acetate: | 0.20% |
| | Sodium pyrrolidonecarboxylate: | 1% (moisturizer) |

Procedure

Add C to B, emulsify B in A at 70° C. and then add D at 60° C., followed by E at 30° C.

EXAMPLE 6

Body Milk

Formula

| | | |
|---|---|---|
| A | Simulsol ™ 165: | 5.0% |
| | Lanol ™ 1688: | 12.0% |
| | Lanol ™ 14M: | 2.0% |
| | Cetyl alcohol: | 0.3% |
| | Scheroemol ™ OP: | 3% |
| B | Water: | qs 100% |
| C | Composition 1: | 0.35% |
| D | Sepicide ™ CI: | 0.2% |
| | Sepicide ™ HB: | 0.5% |
| | Fragrance: | 0.20% |

Procedure

Emulsify B in A at about 75° C.; add C at about 60° C., followed by D at about 30° C.

EXAMPLE 7

O/W Cream

Formula

| | | |
|---|---|---|
| A | Simulsol ™ 165: | 5.0% |
| | Lanol ™ 1688: | 20.0% |
| | Lanol ™ P: | 1.0% (additive with stabilizing effect) |
| B | Water | qs 100% |
| C | Composition 1: | 2.50% |
| D | Sepicide ™ CI: | 0.20% |
| | Sepicide ™ HB: | 0.30% |

Procedure

Introduce B into A at about 75° C., add C at about 60° C., followed by D at about 45° C.

EXAMPLE 8

Non-greasy Antisun Gel

Formula

| | | |
|---|---|---|
| A | Composition 1: | 3.00% |
| | Water: | 30% |
| B | Sepicide ™ CI: | 0.20% |
| | Speicide ™ HB: | 0.30% |
| | Fragrance: | 0.10% |
| C | Dye: | qs |
| | Water: | 30% |
| D | Micropearl ™ M 100: | 3.00% |
| | Water: | qs 100% |
| E | Silicone oil: | 2.0% |
| | Parsol ™ MCX: | 5.00% |

Procedure

Introduce B into A; add C, then D and then E.

EXAMPLE 9

Antisun Milk

Formula

| | | |
|---|---|---|
| A | Sepiperl ™ N: | 3.00% |
| | Sesame oil: | 5.0% |
| | Parsol ™ MCX: | 5.0% |
| | λ-Carrageenan: | 0.10% |
| B | Water: | qs 100% |
| C | Composition 1: | 0.80% |
| D | Fragrance: | qs |
| | Preserving agent: | qs |

Procedure

Emulsify B in A at 75° C., then add C at about 60° C., followed by D at about 30° C. and adjust the pH if necessary.

EXAMPLE 10

Massage Gel

Formula

| | | |
|---|---|---|
| A | Composition 1: | 3.5% |
| | Water: | 20.0% |
| B | Dye: | 2 drops/100 g |
| | Water: | qs |
| C | Alcohol: | 10% |
| | Menthol: | 0.10% |
| D | Silicone oil: | 5.0% |

Procedure

Add B to A; then add C to the mixture, followed by D.

EXAMPLE 11

Massage Care Gel

Formula

| | | |
|---|---|---|
| A | Composition 1: | 3.00% |
| | Water: | 30% |
| B | Sepicide ™ CI: | 0.20% |
| | Sepicide ™ HB: | 0.30% |
| | Fragrance: | 0.05% |
| C | Dye: | qs |
| | Water: | qs 100% |
| D | Micropearl ™ SQL: | 5.00% |
| | Lanol ™ 1688: | 2% |

Procedure

Prepare A; add B, then C and then D.

EXAMPLE 12

Sunburn Gel

Formula

| | | |
|---|---|---|
| A | Composition 1: | 4% |
| | Water: | 30% |
| B | Elastine HPM: | 5.0% |
| C | Micropearl ™ M 100: | 3% |
| | Water: | 5% |
| D | Sepicide ™ CI: | 0.2% |
| | Sepicide ™ HB: | 0.3% |

-continued

| | | |
|---|---|---|
| Fragrance: | | 0.06% |
| 50% sodium Pyrrolidonecarboxylate: | | 1% |
| Water: | | qs 100% |

Procedure

Prepare A; add B, then C and then D.

EXAMPLE 13

Body Milk

Formula

| | | | |
|---|---|---|---|
| A | Sepiperl ™ NL | | 3.0% |
| | Glyceryl triheptonate: | | 10.0% |
| B | Water: | | qs 100% |
| C | Composition 1: | | 1.0% |
| D | Fragrance: | | qs |
| | Preserving agent: | | qs |

Procedure

Melt A at about 75° C. Emulsify B in A at 75° C. and then add C at about 60° C., followed by D.

EXAMPLE 14

Make-up-removing Emulsion Containing Sweet Almond Oil

Formula

| | |
|---|---|
| Montanov ™ 68: | 5% |
| Sweet almond oil: | '5% |
| Water: | qs 100% |
| Composition 1: | 0.3% |
| Glycerol: | 5% |
| Preserving agent: | 0.2% |
| Fragrance: | 0.3% |

EXAMPLE 15

Moisturizing Cream for Greasy Skin

Formula

| | |
|---|---|
| Montanov ™ 68: | 5% |
| Cetylstearyl octanoate: | 8% |
| Octyl palmitate: | 2% |
| Water: | qs 100% |
| Composition 1: | 0.6% |
| Micropearl ™ 100: | 3.0% |
| Mucopolysaccharides: | 5% |
| Sepicide ™ HB: | 0.8% |
| Fragrance: | 0.3% |

EXAMPLE 16

Alcohol-free Soothing after-shave Balm

Formula

| | |
|---|---|
| Mixture of laurylamino acids: | 0.1% to 5% |
| Magnesium potassium aspartate: | 0.002% to 0.5% |
| Lanol ™ 99: | 2% |
| Sweet almond oil: | 0.5% |
| Water: | qs 100% |
| Composition 1: | 3% |
| Sepicide ™ HB: | 0.3% |
| Sepicide ™ CI: | 0.2% |
| Fragrance: | 0.4% |

EXAMPLE 17

Cream Containing HAAs for Sensitive Skin

Formula

| | |
|---|---|
| Mixture of laurylamino acids: | 0.1% to 5% |
| Magnesium potassium aspartate: | 0.002% to 0.5% |
| Lanol ™ 99: | 2% |
| Montanov ™ 68: | 5.0% |
| Water: | qs 100% |
| Composition 1: | 1.50% |
| Gluconic acid: | 1.50% |
| Triethylamine: | 0.9% |
| Sepicide ™ HB: | 0.3% |
| Sepicide ™ CI: | 0.2% |
| Fragrance: | 0.4% |

EXAMPLE 18

After-sun Soothing Care Product

Formula

| | |
|---|---|
| Mixture of laurylamino acids: | 0.1% to 5% |
| Magnesium potassium aspartate: | 0.002% to 0.5% |
| Lanol ™ 99: | 10.0% |
| Water: | qs 100% |
| Composition 1: | 2.50% |
| Sepicide ™ HB: | 0.3% |
| Sepicide ™ CI: | 0.2% |
| Fragrance: | 0.4% |
| Dye: | 0.03% |

EXAMPLE 19

Make-up Removing Milk

Formula

| | |
|---|---|
| Sepiperl ™ N: | 3% |
| Primol ™ 352: | 8.0% |
| Sweet almond oil: | 2% |
| Water: | qs 100% |
| Composition 1: | 0.8% |
| Preserving agent: | 0.2% |

EXAMPLE 20

Body Milk

Formula

| | |
|---|---|
| Sepiperl ™ N: | 3.5% |
| Lanol ™ 37T: | 8.0% |
| Solagum ™ L: | 0.05% |
| Water: | qs 100% |
| Benzophenone: | 2.0% |
| Dimethicone 350 cPs: | 0.05% |
| Composition 1: | 0.08% |
| Preserving agent: | 0.2% |
| Fragrance: | 0.4% |

EXAMPLE 21

Liquid Foundation

Formula

| | |
|---|---|
| Simulsol ™ 165: | 5.0% |
| Lanol ™ 84D: | 8.0% |
| Lanol ™ 99: | 5.0% |
| Water: | qs 100% |
| Mineral pigments and fillers: | 10.0% |
| Composition 1: | 1.2% |
| Preserving agent: | 0.2% |
| Fragrance: | 0.4% |

EXAMPLE 22

Antisun Milk

Formula

| | |
|---|---|
| Sepiperl ™ N: | 3.5% |
| Lanol ™ 37T: | 10.0% |
| Parsol NOX ™: | 5.0% |
| Eusolex ™ 4360: | 2.0% |
| Water: | qs 100% |
| Composition 1: | 1.8% |
| Preserving agent: | 0.2% |
| Fragrance: | 0.4% |

EXAMPLE 23

Gel for the Contour of the Eyes

Formula

| | |
|---|---|
| Composition 1: | 2.0% |
| Fragrance: | 0.06% |
| Sodium pyrrolidonecarboxylate: | 0.2% |
| Dow Corning ™ 245 fluid: | 2.0% |
| Water: | qs 100% |

EXAMPLE 24

Leave-on Care Composition

Formula

| | |
|---|---|
| Composition 1: | 1.5% |
| Fragrance: | qs |
| Preserving agent: | qs |
| Dow Corning ™ X2 8360: | 5.0% |
| Dow Corning ™ Q2 1401: | 15% |
| Water: | qs 100% |

EXAMPLE 25

Slendering Gel

| | |
|---|---|
| Composition 1: | 5% |
| Ethanol: | 30% |
| Menthol: | 0.1% |
| Caffeine: | 2.5% |
| Extract of Ruscus: | 2% |
| Extract of English ivy: | 2% |
| Sepicide ™ HP: | 1% |
| Water: | qs 100% |

EXAMPLE 26

Alcohol-free Soothing After-shave Balm

Formula

| | | |
|---|---|---|
| A | Lipacid ™ PVB: | 1.0% |
| | Lanol ™ 99: | 2.0% |
| | Sweet almond oil: | 0.5% |
| B | Composition 1: | 3.5% |
| C | Water: | qs 100% |
| D | Fragrance: | 0.4% |
| | Sepicide ™ HB: | 0.4% |
| | Sepicide ™ CI: | 0.2% |

EXAMPLE 27

After-shave Refreshing Gel

Formula

| | | |
|---|---|---|
| A | Lipacid ™ PVB: | 0.5% |
| | Lanol ™ 99: | 5.0% |
| | Composition 1: | 2.5% |
| B | Water: | qs 100% |
| C | Micropearl ™ LM: | 0.5% |
| | Fragrance: | 0.2% |
| | Sepicide ™ HB: | 0.3% |
| | Sepicide ™ CI: | 0.2% |

EXAMPLE 28

Care Products for Greasy Skin

Formula

| | | |
|---|---|---|
| A | Micropearl ™ M 310: | 1.0% |
| | Composition 1: | 5.0% |
| | Octyl isononanoate: | 4.0% |
| B | Water: | qs 100% |
| C | Sepicontrol ™ A5: | 4.0% |
| | Fragrance: | 0.1% |
| | Sepicide ™ HB: | 0.3% |
| | Sepicide ™ CI: | 0.2% |
| D | Capigel ™ 98: | 0.5% |
| | Water: | 10% |

EXAMPLE 29

Cream Containing HAAs

Formula

| | | |
|---|---|---|
| A | Montanov ™ 68: | 5.0% |
| | Lipacid ™ PVB: | 1.05% |
| | Lanol ™ 99: | 10.0% |
| B | Water: | qs 100% |
| | Gluconic acid: | 1.5% |
| | TEA (triethylamine): | 0.9% |
| C | Composition 1: | 1.5% |
| D | Fragrance: | 0.4% |
| | Sepicide ™ HB: | 0.2% |
| | Sepicide ™ CI: | 0.4% |

EXAMPLE 30

Non-greasy Self-tanning Agent for the Face and Body

Formula

| | | |
|---|---|---|
| A | Lanol ™ 2681: | 3.0% |
| | Composition 1: | 2.5% |
| B | Water: | qs 100% |
| | Dihydroxyacetone: | 3.0% |
| C | Fragrance: | 0.2% |
| | Sepicide ™ HB: | 0.8% |
| | NaOH (sodium hydroxide): | qs pH = 5% |

EXAMPLE 31

Antisun Milk Containing Tahitian Perfumed oil

Formula

| | | |
|---|---|---|
| A | Tahitian perfumed oil: | 10% |
| | Lipacid ™ PVB: | 0.5% |
| | Composition 1: | 2.2% |
| B | Water: | qs 100% |
| C | Fragrance: | 0.1% |
| | Sepicide ™ HB: | 0.3% |
| | Sepicide ™ CI: | 0.1% |
| | Octyl methoxycinnamate: | 4.0% |

EXAMPLE 32

Antisun Care Product for the Face

Formula

| | | |
|---|---|---|
| A | Cyclomethicone and dimethiconol: | 4.0% |
| | Composition 1: | 3.5% |
| B | Water: | qs 100% |
| C | Fragrance: | 0.1% |
| | Sepicide ™ HB: | 0.1% |
| | Sepicide ™ CI: | 0.21% |
| | Octyl methoxycinnamate: | 5.0% |
| | Titanium mica: | 2.0% |
| | Lactic acid: | qs pH = 6.5 |

EXAMPLE 33

Self-tanning Emulsion

Formula

| | | |
|---|---|---|
| A | Lanol ™ 99: | 15% |
| | Montanov ™ 68: | 5.0% |
| | Octyl para-methoxycinnamate: | 3.0% |
| B | Water: | qs 100% |
| | Dihydroxyacetone: | 5.0% |
| | Monosodium phosphate: | 0.2% |
| C | Composition 1: | 0.5% |
| D | Fragrance: | 0.3% |
| | Sepicide ™ HB: | 0.8% |
| | NaOH: | qs pH = 5 |

The commercial names given above have the following definitions:

Montanov™ 68 (cetearyl glucoside) is a self-emulsifying composition as described in WO 92/06778, sold by the company SEPPIC.

Micropearl™ M 100 is an ultrafine powder which feels very soft and has a matt effect, sold by the company Matsumo.

Sepicide™ CI, imidazolineurea, is a preserving agent sold by the company SEPPIC.

Pemulen™ TR is an acrylic polymer sold by Goodrich.

Simulsol™ 165 is self-emulsifying glyceryl stearate sold by the company SEPPIC.

Lanol™ 1688 is an emollient ester with a non-greasy effect, sold by the company SEPPIC.

Lanol™ 14M and Lanol™ S are consistency factors sold by the company SEPPIC.

Sepicide™ HB, which is a mixture of phenoxyethanol, methyl paraben, ethyl paraben, propyl paraben and butyl paraben, is a preserving agent sold by the company SEPPIC.

Monteine™ CA is a moisturizer sold by the company SEPPIC.

Schercemol™ OP is an emollient ester with a non-greasy effect.

Lanol™ P is an additive with a stabilizing effect, sold by the company SEPPIC.

Parsol™ MCX is octyl para-methoxycinnamate, sold by the company Givaudan.

Sepiperl™ N is a nacreous agent sold by the company SEPPIC, based on a mixture of alkyl polyglucosides such as those described in WO 95/13863.

Microperl™ SQL is a mixture of microparticles containing squalane which is released under the action of massaging; it is sold by the company Matsumo.

Lanol™ 99 is isononyl isononanoate, sold by the company SEPPIC.

Lanol™ 37T is glyceryl triheptanoate, sold by the company SEPPIC.

Solagum™ L is a carrageenan sold by the company SEPPIC.

Marcol™ 82 is a liquid paraffin sold by the company Esso.

Lanol™ 84D is dioctyl malate, sold by the company SEPPIC.

Parsol NOX™ is a sunscreen sold by the company Givaudan.

Eusolex™ 4360 is a sunscreen sold by the company Merck.

Dow Corning™ 245 fluid is cyclomethicone, sold by the company Dow Corning.

Lipacid™ PVB is a palmitoylated wheat protein hydrolysate sold by the company SEPPIC.

Micropearl™ LM is a mixture of squalane, poly(methyl methacrylate) and menthol, sold by the company SEPPIC.

Sepicontrol™ A5 is a mixture of capryloylglycine, sarcosine and extract of Cinnamon zylanicum, sold by the company SEPPIC, such as those described in international patent application PCT/FR98/01313, filed on Jun. 23, 1998.

Capigel™ 98 is an acrylate copolymer sold by the company SEPPIC.

Lanol™ 2681 is a coconut caprate/caprylate mixture sold by the company SEPPIC.

What is claimed is:

1. Composition consisting essentially of:

an oil phase, an aqueous phase, at least one water-in-oil (W/O) emulsifier, and at least one oil-in-water (O/W) emulsifier, said composition being an inverted latex consisting of from 20% to 70% by weight of a branched or crosslinked anionic polyelectrolyte of acrylic acid which is partially or totally salinized as an ammonium salt;

said composition containing from 2.5% to 15% by weight, of emulsifiers, among which from 20% to 50%, of the total weight of the emulsifiers present are water-in-oil (W/O) emulsifiers, and among which from 80% to 50%, are oil-in-water (O/W) emulsifiers, said crosslinking agent and/or branching agent being sodium diallyloxyacetate; and said oil phase representing from 15% to 40% of the total weight of the composition.

2. Composition as defined in claim 1 comprising from 25% to 40% by weight of branched or crosslinked anionic polyelectrolyte.

3. Composition as defined in claim 1, in which the crosslinking agent and/or branching agent is used in a molar proportion, expressed relative to the monomers used, from 0.05% to 0.5%.

4. Composition as defined in claim 1, in which the water-in-oil emulsifier is chosen from sorbitan monooleate or sorbitan isostearate.

5. Composition as defined in claim 1, in which the oil-in-water emulsifier is chosen from sorbitan oleate ethoxylated with 20 moles of ethylene oxide, castor oil ethoxylated with 40 mol of ethylene oxide, sorbitan laurate ethoxylated with 20 moles of ethylene oxide or lauryl alcohol ethoxylated with 7 moles of ethylene oxide.

6. Composition as defined in claim 1, in which the oil phase represents from 20% to 25%, of its total weight.

7. Composition as defined in claims 1, in which the oil phase comprises isohexadecane or a white mineral oil.

8. Cosmetic, dermopharmaceutical or pharmaceutical composition comprising from 0.1% to 10% by weight of a reverse latex as defined in claim 1.

9. Composition as defined in claim 1, wherein, said composition contains from 4% to 9% by weight of emulsifiers.

10. Composition as defined in claim 9, wherein, from 25% to 40% of the total weight of the emulsifiers present are water-in-oil (W/O) emulsifiers.

11. Composition of claim 3, wherein, the crosslinking agent and/or branching agent is used in a molar proportion, expressed relative to the monomers used, from 0.1% to 0.25%.

* * * * *